United States Patent [19]

O'Lenick, Jr. et al.

[11] Patent Number: 5,196,589

[45] Date of Patent: Mar. 23, 1993

[54] STABILIZED ACRYLONITRILE POLYMERIZATIONS

[75] Inventors: Anthony J. O'Lenick, Jr., Lilburn, Ga.; J. Michael Clumpner, Delavan, Wis.

[73] Assignee: LCE Partnership, Janesville, Wis.

[21] Appl. No.: 760,335

[22] Filed: Sep. 16, 1991

[51] Int. Cl.$^5$ ............................................. C07C 209/48
[52] U.S. Cl. .................................. 564/493; 564/490; 564/491; 564/503; 564/505; 564/508; 564/511; 558/448; 558/450; 558/452; 558/467
[58] Field of Search ............... 564/490, 491, 493, 503, 564/505, 508, 511; 558/448, 450, 452, 467

[56] References Cited

U.S. PATENT DOCUMENTS

| | | | |
|---|---|---|---|
| 4,670,131 | 6/1987 | Ferrell | 585/950 |
| 4,967,006 | 10/1990 | Carr | 564/491 |
| 5,081,305 | 1/1992 | Carr et al. | 564/491 |

OTHER PUBLICATIONS

Wang et al., *Chem. Abs.*, 100:58167r (1988).
Wang et al., *Chem. Abs.*, 115:280613v (1991).
Wang et al., *Chem. Abs.*, 108:94970g (1987).
Czajlik et al., *Chem. Abs.*, 88:51211u (1977).
Zaitsev et al., *Chem. Abs.*, 88:38214c (1977).
Bailey, *Chem. Abs.*, 70:3261s (1968).

*Primary Examiner*—Glennon H. Hollrah
*Assistant Examiner*—Scott C. Rand

[57] ABSTRACT

The present invention relates to novel methods of stabilizing polymers of acrylonitrile. The polymers are stabilized by the inclusion of small amounts of stable free radicals compounds which act to inhibit the homopolymerization of the acrylonitrile while promoting the reaction of the acrylonitrile with nucleophilic species such as amines and alcohols.

13 Claims, No Drawings

STABILIZED ACRYLONITRILE POLYMERIZATIONS

FIELD OF INVENTION

The present invention relates to novel methods of stabilizing polymers of acrylonitrile. The polymers are stabilized by the inclusion of small amounts of stable free radicals compounds which act to inhibit the homopolymerization of the acrylonitrile while promoting the reaction of the acrylonitrile with nucleophilic species such as amines and alcohols. The products prepared by this novel process will have fewer undesirable by products giving lighter color, higher amine values, higher primary amine content, lower hydroxyl values which are indications of the greater reaction efficiencies. The process is shorter in duration and substantial reduction in catalyst poisoning in the hydrogenation step. This process with its inherent lower polyacrylonitrile content allows for the elimination of a washing step practiced in the older processes, prior to hydrogenation.

BACKGROUND OF THE INVENTION

It is highly desirable to be able to produce pure amines and polyamines by the reaction of acrylonitrile with alcohols or amines. While the reaction of the amines and alcohols and other nucelophilic species with acrylonitrile proceeds, another competitive reaction, namely free radical polymerization also occurs to varying extents. This results in polyacrylonitrile adducts and lower amounts of acrylonitrile added to the amine or alcohol. The problem is worse when alcohols, amines or polyoxyalkylene glycol raw materials are solid at reaction temperatures. The increasing of reaction temperatures to obtain liquid reactants, results in a major increase of polyacrylonitrile produced. This has resulted in the cyanoethylation reaction with acrylonitrile being of limited use for either high viscosity, high molecular weight or solid reactants. The current invention overcomes these limitations by allowing for the use of elevated temperatures during reaction and little or no polymerization of acrylonitrile. The polymerization reaction is effectively stopped, even at elevated temperatures, by the addition of a specific class of free radical inhibitors. As previously stated, the products prepared by this novel process will have fewer undesirable by products giving lighter color, higher amine values, higher primary amine content, lower hydroxyl values which are indications of the greater reaction efficiencies. The process is shorter in duration and substantial reduction in catalyst poisoning in the hydrogenation step. This process with its inherent lower polyacrylonitrile content allows for the elimination of a washing step practiced in the older processes, prior to hydrogenation.

Reaction Sequence 1   Nucleophilic Addition

A. Amines

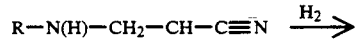

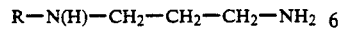

Desired Product (diamine)

B. Alcohols

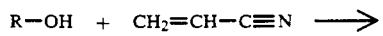

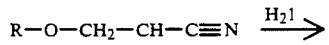

$$R-O-CH_2-CH_2-CH_2-NH_2$$

Desired Product (ether amine)

C. Polyglycols

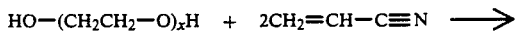

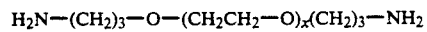

Reaction Sequence 2   Free Radical Polymerization

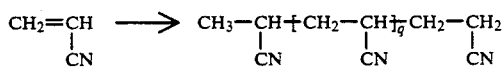

(undesired reaction)

It is known that acrylonitrile is very reactive and will polymerize easily. In cases were it is desirable to react the acrylonitrile in a free radical reaction, this polymerization results in loss of reactive raw material and undesired by products. Prior to the compositions of the present invention, low temperature of reaction was used to minimize the rate of homopolymerization of acrylonitrile. This results in two drawbacks. First not only does the rate of homopolymerization slow, but the rate of the desired reaction also slows. Second, there is a limitation on the type of reactant which can be reacted. Only low viscosity materials react effectively to give the desired nucleophilic adduct. Materials which are solids, high molecular weight or viscous liquids at the lower reaction temperatures cannot be used in the process. This imposes a practical limit on the type of product which can be cyanoethylated using acrylonitrile.

We have found that the addition of small amounts of stable free radical compounds to the starting amine or alcohol prior to commencing the reaction to make the ether amine or diamine, effectively eliminates the free radical polymerization of the acrylonitrile and has no effect upon the desired cyanoethylation (reaction sequence 1). Reaction sequences can now be conducted at higher temperatures allowing for cyanoethylation of materials heretofore impossible or difficult to react prior to the compositions of the present invention.

Reaction conditions, rates and purity are all major concerns when reproducible high purity amines or ether amines are desired. The use of stable free radical compounds has surprisingly been found to be effective in preventing the undesired free radical polymerization of acrylonitrile.

A variety of "standard antioxidants" have been shown to inhibit or retard vinyl polymerization. The commonly used inhibitors appear to function by reacting in some manner with an initiator radical to yield a species of lower reactivity that results in a lower tendency to continue chain propagation. These "standard antioxidants", which are ineffective in our invention, include phenols, quinones, aromatic nitro and nitroso compounds, amines and thiol compounds.

Stable free radicals have been known for many years and exists in the patent literature, but have been used primarily, if not exclusively in the prevention of polymerization in vinyl reactive systems U.S. Pat. No. 4,670,131 issued to Ferrell discloses the use of stable free radical compounds in the prevention of polymerization of olefinic materials. This process relates to the reaction of a vinyl containing material to make a saturated higher molecular weight species. Clearly, this reaction has been understood in terms of free radical chemistry. Free radical inhibitors or scavengers inhibit or retard the polymerization of chain propagating reactions in vinyl monomer systems. The mechanism is thought to be a scavenger of the free radicals which form on the monomer. Since the free radical scavenger is stable, it reacts rapidly with free radicals of the monomer, which form in low concentrations.

In addition to abstraction, several compounds retard vinyl polymerization by radical addition which again produces a radical species which is not reactive toward the monomer. Quinone type inhibitors are probably the best example of this kind of inhibition mechanism.

It is appreciated that the free radical reaction process is not inhibited by the typical vinyl inhibitors like phenols, quinones, aromatic nitro and nitroso compounds, amines and thiol compounds. We have discovered that in order to develop an inhibitor for acrylonitrile reactions, a different type of approach must be employed. Stable free radicals, such as NOVA INHIBITOR 469, (a nitroxyl type stable free radical) provide such a system. These stable free radicals are far too stable to initiate polymerization, but their free electron is available to immediately react with any radical initiator, rendering the potential initiator totally inactive. This class of inhibitors has been found to be effective in preventing acrylonitrile polymerization, a free radical type reaction, but has no effect upon the desired nucleophilic reaction.

The preferred stable free radical is a nitroxyl.

OBJECT OF THE INVENTION

It is the objective of this invention to provide stable acrylonitrile compositions with improved stability as relates to homopolymerization.

Additionally, the present invention is directed to a process for the preparation of higher purity ether amines and polyamines which are made by the nucleophilic reaction of an alcohol or amine with acrylonitrile. This is accomplished by the inhibition of the homopolymerization of acrylonitrile which is a free radical reaction. This inhibition is accomplished by incorporation of an effective inhibitory concentration of a stable free radical.

Another object of the present invention is the development of a higher temperature process for cyanoethylation of materials which have elevated melting points. Such materials include polyalkylene glycols and high molecular weight alkyl alcohols and their alkoxylates and amines and their alkoxylates. By polyalkylene glycol is meant polyethylene glycol, polypropylene glycol, polybutylene glycol and mixtures thereof.

THE INVENTION

The present application relates to a novel method of producing high purity ether amines or polyamines. The raw material compounds, i.e. the alcohol or amine have incorporated into them, from before the time of reaction with the acrylonitrile, a free radical type inhibitor which significantly retards the homopolymerization of acrylonitrile.

Stable free radicals useful in the process of the present invention are described in U.S. Pat. No. 3,481,953; U.S. Pat. No. 3,489,522; U.S. Pat. No. 3,507,867 and U.S. Pat. No. 3,453,288. They are marketed by Aldrich as Doxyl and Proxyl Spin Labels. Some examples are;
Doxyl-cyclohexane (Aldrich #29,397-7),
5 Doxyl-decane (Aldrich #29,399-7),
3-(Aminomethyl)-proxyl (Aldrich #27,018-0),
2-(acetomercurl)-4,4,5,5-tetramethyl-2imidazolin-1yloxy-3-(Aldrich #25,325-9),
Di-tert-butyl nitroxide,
galvinoxyl,
2,2-diphenyl-1-picrylhydrazyl hydrate,
bisphenylene-B-phenylallyl,
3-carbamoyl-2,2,5,5-tetramethyl-3-pryrrolin-1-yloxy, The most effective product tested is available form Nova Molecular Technology Lake Geneva Wisconsin and is sold under the trade name NOVA INHIBITOR 469 (a nitroxyl type stable free radical).

We have incorporated these materials into the alcohol or amine raw materials used to react with acrylonitrile, prior to heat up and have found that not only do we obtain less byproducts, we also get a product with a more stable molecular weight.

In order to show this, we prepared several ether amines and polyamines using the process and compositions envisioned by the present invention and the same compounds using the standard processes utilized before the current invention.

EXAMPLES

General Procedure

The ether amines and polyamines may be prepared from alcohols or amines respectively by a process which includes as a first step the cyanoethylation of the alcohol or amine with acrylonitrile in the presence of an alkaline catalyst, e.g., benzyltrimethylammonium hydroxide, potassium hydroxide, sodium methoxide, or sodium hydroxide, to form B-alkoxypropionitrile. The alcohol or amine and acrylonitrile may be reacted at temperatures between about 25 C., and about 80 C., in the presence of about 0.1 percent potassium hydroxide for a period of about five to about six hours. The reaction is generally exothermic.

The B-alkoxypropionitrile is then hydrogenated in the presence of a suitable catalyst, e.g., Raney nickel, to form an alkoxypropylamine. The hydrogenation of the oxypropionitrile is preferably carried out at a temperature of 125 C., with a hydrogen partial pressure of about 300 psig.

Polyglycol Reactions (to make the bis ether amine)

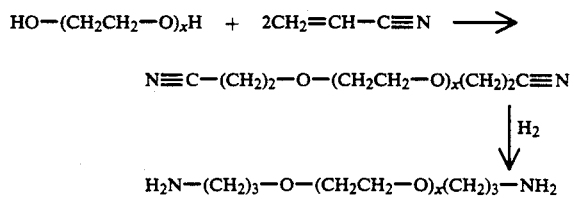

EXAMPLE 1

Add 3,350 grams of polyethylene glycol having a molecular weight of 3350. (Such a material is commercially available from Alkaril Chemicals Inc. Winder Ga and is sold as Alkapol PEG 3350). Next add 1.0 grams of potassium hydroxide. 107.0 grams of acrylonitrile is next added with cooling to keep the reaction temperature at 60 C.. The reaction mixture is held for a period of about five to about ten hours. The reaction is generally exothermic and requires good cooling.

The nitrile is then hydrogenated in the presence of Raney nickel with two equivalents of hydrogen, to form an alkoxypropylamine. The hydrogenation of the oxypropionitrile is carried out at 130 C., with a hydrogen partial pressure of about 300 psig and ammonia partial pressure of about 150 psig.

EXAMPLES 2-9

Example 1 was repeated, however this time adding the specified amount of the specified stable free radical inhibitor the polyethylene glycol reactant prior to the addition of the acrylonitrile.

| Example # | Type of Stable Free Radical | Concentration (ppm) |
|---|---|---|
| 2 | Di-tert-butyl nitroxide, | 100 |
| 3 | Hydroquinone monomethylether (a non stable free radical inhibitor) Not a compound of the present invention | 100 |
| 4 | 2,2-diphenyl-1-picrylhydrazyl hydrate, | 100 |
| 5 | Bisphenylene-B-phenylallyl, | 100 |
| 6 | NOVA INHIBITOR 469 (a nitroxyl type stable free radical) | 100 |
| 7 | Di-tert-butyl nitroxide | 10 |
| 8 | NOVA INHIBITOR 469 (a nitroxyl type stable free radical) | 10 |
| 9 | NOVA INHIBITOR 469 (a nitroxyl type stable free radical) | 1 |

| EFFICIENCY OF REACTION (Reduction of Hydroxyl Value) ||
|---|---|
| Example | % Reaction |
| 1 | 58.2 |
| 2 | 98.6 |
| 3 | 61.1 |
| 4 | 78.6 |
| 5 | 84.8 |
| 6 | 86.2 |
| 7 | 85.1 |
| 8 | 83.1 |
| 9 | 79.1 |

As can be seen the molecular weight achieved is enhanced by incorporation of the stable free radical. This is because the stable free radical minimizes side reactions and by products.

Alcohol Reactions (to make the ether amine)

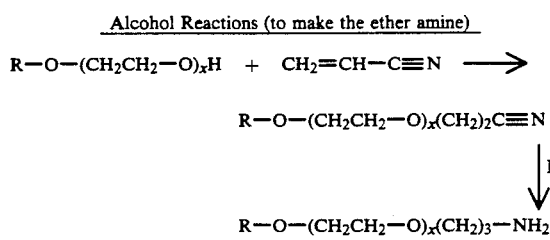

EXAMPLE 10

Add 270.5 grams of stearyl alcohol. Next add 1.0 grams of potassium hydroxide. 54.0 grams of acrylonitrile is next added with cooling to keep the reaction temperature at 60° C. The reaction mixture is held for a period of about five to about six hours. The reaction is generally exothermic and requires good cooling.

The nitrile is then hydrogenated in the presence of Raney nickel with two equivalents of hydrogen, to form an alkoxypropylamine. The hydrogenation of the oxypropionitrile is carried out at 130° C., with a hydrogen partial pressure of about 300 psig and an ammonia partial pressure of 150 psig.

EXAMPLES 11-19

Example 10 was repeated, however this time adding the specified amount of the specified stable free radical inhibitor the stearyl alcohol reactant prior to the addition of the acrylonitrile.

As can be seen the molecular weight achieved is enhanced by incorporation of the stable free radical. This is because the stable free radical minimizes side reactions and by products.

| Example # | Type of Stable Free Radical | Concentration (ppm) |
|---|---|---|
| 11 | Di-tert-butyl nitroxide, | 100 |
| 12 | Hydroquinone monomethylether (a non stable free radical inhibitor) Not a compound of the present invention | 100 |
| 13 | 2,2-diphenyl-1-picrylhydrazyl hydrate, | 100 |
| 14 | Bisphenylene-B-phenylallyl, | 100 |
| 15 | NOVA INHIBITOR 469 (a nitroxyl type stable free radical) | 100 |
| 16 | Di-tert-butyl nitroxide | 10 |
| 17 | NOVA INHIBITOR 469 (a nitroxyl type stable free radical) | 10 |
| 18 | NOVA INHIBITOR 469 (a nitroxyl type stable free radical) | 1 |
| 19 | NOVA INHIBITOR 469 (a nitroxyl type stable free radical) | 5 |

| EFFICIENCY OF REACTION (By reduction of Hydroxyl Value) ||
|---|---|
| Example | % Reaction |
| 10 | 68.2 |
| 11 | 98.6 |
| 12 | 68.1 |
| 13 | 88.6 |
| 14 | 89.8 |
| 15 | 88.2 |
| 16 | 89.1 |
| 17 | 89.1 |
| 18 | 83.1 |
| 19 | 85.5 |

As can be seen the molecular weight achieved is enhanced by incorporation of the stable free radical. This is because the stable free radical minimizes side reactions and by products.

AMINE REACTIONS (TO MAKE THE POLYAMINES)

EXAMPLE 20

Add 270.0 grams of stearyl amine. Next add 1.0 grams of potassium hydroxide. 54.0 grams of acrylonitrile is next added with cooling to keep the reaction temperature at 60° C. The reaction mixture is held for a period of about five to about six hours. The reaction is generally exothermic and without good cooling.

The nitrile is then hydrogenated in the presence of Raney nickel with two equivalents of hydrogen, to form an alkoxypropylamine. The hydrogenation of the oxypropionitrile is carried out at 130 C., with a hydrogen partial pressure of about 300 psig and a ammonia partial pressure of 150 psig.

EXAMPLE 21-28

Example 20 is only this time adding the specified amount of the specified free radical inhibitor before heating up the reaction mass.

| Example # | Type of Stable Free Radical | Concentration (ppm) |
|---|---|---|
| 21 | Di-tert-butyl nitroxide, | 100 |
| 22 | Hydroquinone monomethylether (a non stable free radical inhibitor) Not a compound of the present invention | 100 |
| 23 | 2,2-diphenyl-1-picrylhydrazyl hydrate, | 100 |
| 24 | Bisphenylene-B-phenylallyl, | 100 |
| 25 | NOVA INHIBITOR 469 (a nitroxyl type stable free radical) | 100 |
| 26 | Di-tert-butyl nitroxide | 10 |
| 27 | NOVA INHIBITOR 469 (a nitroxyl type stable free radical) | 10 |
| 28 | NOVA INHIBITOR 469 (a nitroxyl type stable free radical) | 1 |

EFFICIENCY OF REACTION
(Measured by Primary and Secondary amine)

| Example | % Reaction |
|---|---|
| 20 | 81.2 |
| 21 | 97.6 |
| 22 | 81.9 |
| 23 | 93.8 |
| 24 | 95.8 |
| 25 | 90.2 |
| 26 | 98.1 |
| 27 | 96.1 |
| 28 | 94.1 |

As can be seen the molecular weight achieved is enhanced by incorporation of the stable free radical. This is because the stable free radical minimizes side reactions and by products.

What is claimed is:

1. A process for the preparation of an polyamine which comprises the reaction of;
    (a) a primary alkyl amine, said primary alkyl amine compound having had between 1 and 100 parts per million of a stable free radical compound added;
    (b) acrylonitrile;
    (c) an alkaline catalyst selected from group consisting of benzyltrimethylammonium hydroxide, potassium hydroxide, sodium methoxide, and sodium hydroxide; and
    (d) in a subsequent step, reaction with hydrogen in the presence of a hydrogenation catalyst.

2. A process of claim 1 wherein the amine compound is an alkyl amine having from 6 to 36 carbon atoms.

3. A process of claim 1 wherein the stable free radical is a nitroxyl.

4. A process of claim 1 wherein the stable free radical is di-tert-butyl nitroxide.

5. A process for the preparation of a polyalkylene glycol based amine which comprises the reaction of;
    (a) a polyalkylene glycol compound, said polyalkylene glycol compound having had between 1 and 100 parts per million of a stable free radical compound added;
    (b) acrylonitrile;
    (c) an alkaline catalyst selected from the group consisting of benzyltrimethylammonium hydroxide, potassium hydroxide, sodium methoxide, and sodium hydroxide; and
    (d) in a subsequent step, reaction with hydrogen in the presence of a hydrogenation catalyst.

6. A process of claim 5 wherein the stable free radical is a nitroxyl.

7. A process of claim 5 wherein the stable free radical is di-tert-butyl nitroxide.

8. A process for the preparation of an ether amine composition which comprises the reaction of;
    (a) an alkanol compound, said alkanol compound having had between 1 and 100 parts per million of a stable free radical compound added;
    (b) acrylonitrile;
    (c) an alkaline catalyst selected from the group consisting of benzyltrimethylammonium hydroxide, potassium hydroxide, sodium methoxide, and sodium hydroxide; and
    (d) in a subsequent step, reaction with hydrogen in the presence of a hydrogenation catalyst.

9. A process of claim 8 wherein the alkanol compound is an has from 6 to 36 carbon atoms.

10. A process of claim 8 wherein the stable free radical is a nitroxyl.

11. A process of claim 8 wherein the stable free radical is di-tert-butyl nitroxide.

12. A process of claim 8 wherein the alkanol contains from 8 to 18 carbon atoms.

13. A process of claim 8 wherein the alkanol contains 12 carbon atoms.

* * * * *